(12) United States Patent
Laborie et al.

(10) Patent No.: US 7,232,505 B2
(45) Date of Patent: Jun. 19, 2007

(54) METHOD OF REGENERATING AN AQUEOUS GLYCOL SOLUTION CONTAINING SALTS

(75) Inventors: Géraldine Laborie, Courbevoie (FR); Fabrice Lecomte, Rueil Malmaison (FR); Chantal Rigaill, Yerres (FR); Lionel Waintraub, Saint Mande (FR)

(73) Assignees: Institut Francais du Petrole, Rueil Malmaison Cedex (FR); Prosernat, Paris la Defense Cedex (FR)

( * ) Notice: Subject to any disclaimer, the term of this patent is extended or adjusted under 35 U.S.C. 154(b) by 257 days.

(21) Appl. No.: 10/691,508

(22) Filed: Oct. 24, 2003

(65) Prior Publication Data
US 2005/0072663 A1 Apr. 7, 2005

(30) Foreign Application Priority Data
Oct. 28, 2002 (FR) .................................. 02 13425

(51) Int. Cl.
*B01D 3/10* (2006.01)
*C07C 27/28* (2006.01)
*C07C 29/80* (2006.01)

(52) U.S. Cl. ............................ 203/18; 203/47; 203/91; 203/98; 203/DIG. 9; 210/710; 210/768; 210/774; 568/868; 568/916

(58) Field of Classification Search .................. 203/18, 203/47, 91, 98, DIG. 9; 210/710, 768, 774, 210/790; 568/868, 916
See application file for complete search history.

(56) References Cited

U.S. PATENT DOCUMENTS

| 3,726,929 | A | * | 4/1973 | Payne et al. ................. 568/778 |
| 4,427,507 | A | | 1/1984 | van Aken et al. ........... 204/151 |
| 6,444,095 | B1 | * | 9/2002 | Evans et al. ................. 202/174 |
| 6,793,714 | B2 | * | 9/2004 | Lecomte et al. ............... 95/174 |

FOREIGN PATENT DOCUMENTS

GB  2 084 885  * 4/1982

OTHER PUBLICATIONS

Preliminary Search Repord dated Jul. 25, 2003.

* cited by examiner

*Primary Examiner*—Virginia Manoharan
(74) *Attorney, Agent, or Firm*—Antonelli, Terry, Stout & Kraus, LLP.

(57) ABSTRACT

Method of regenerating a glycol solution containing water, hydrocarbons and salts. The glycol solution is expanded in drum (2), then distilled in column (7). The concentrated glycol collected at the level of reboiler (8) is placed under vacuum to vaporize the water and to precipitate the salts. The salts are separated from the glycol in separation device (13). The concentrated glycol freed of the salts is stored in capacity (16).

12 Claims, 3 Drawing Sheets

METHOD OF REGENERATING AN AQUEOUS GLYCOL SOLUTION CONTAINING SALTS

FIELD OF THE INVENTION

The present invention relates to the technical field of regeneration of an aqueous glycol solution containing salts, and more particularly monoethylene glycol (MEG) used for natural gas transportation.

BACKGROUND OF THE INVENTION

Natural gas at the outlet of production wells is often associated with formation water containing dissolved salts (sodium chlorides, potassium chlorides, calcium chlorides, sodium bicarbonates, etc.). The natural gas is transported from the production site to a processing site by circulation in lines. If the natural gas is water-saturated and at equilibrium with an aqueous phase, depending on the transportation conditions (pressure and temperature), hydrate plugs are likely to form which may lead to production stop. To avoid such problems, a hydrate inhibitor such as glycol is injected into the pipelines. An aqueous solution containing between 60% and 90% by weight of glycol can be used. After transportation, a mixture consisting of formation water and glycol is recovered, then processed in a glycol regeneration plant in order to reconcentrate the glycol, i.e. to remove the water. The regenerated glycol can again be injected into the pipelines carrying the natural gas.

Glycol distillation systems for separating the glycol from the water-glycol mixture are known to the man skilled in the art. In general, the systems of the prior art allow to obtain an aqueous solution containing between 70% and 90% glycol.

However, regeneration of the glycol leads to concentrate the salts, initially present in the formation water, in the regenerated glycol. Salt concentration is the cause of operating problems such as salt accumulation on certain parts of the regeneration device, thus reducing the efficiency thereof, and such as corrosion of the regeneration device.

The present invention provides a method of regenerating an aqueous glycol solution allowing to remove part of the water, as well as the salts.

The solubility of the salts in aqueous glycol solutions varies with the temperature and the water content of the solution. Adjusting the temperature and lowering the water content allows the solubility of the salts in aqueous glycol solutions to be reduced. It is thus possible to cause precipitation of the salts, the precipitated salts being then separated from the aqueous glycol solution.

SUMMARY OF THE INVENTION

Generally speaking, the invention relates to a method of regenerating a glycol solution containing water, hydrocarbons and dissolved salts, comprising the following stages:

a) expanding said solution so as to release hydrocarbons and to obtain a hydrocarbon-poor solution, b) distilling in a distillation column the hydrocarbon-poor solution obtained in stage a) to obtain a glycol-enriched solution and a vapour comprising water and hydrocarbons, c) placing under vacuum a first part of the glycol-enriched solution obtained in stage b) under a pressure below 90,000 Pa abs. to obtain vaporized water and a glycol solution comprising precipitated salts, d) separating the precipitated salts from the glycol solution obtained in stage c) to obtain precipitated salts and a salt-depleted glycol solution.

The method according to the invention can also comprise the following stages:

e) placing under vacuum the salt-depleted glycol solution obtained in stage d) under a pressure below 50,000 Pa abs. to obtain vaporized water and a glycol solution comprising precipitated salts, f) separating the precipitated salts from the glycol solution obtained in stage e) to obtain precipitated salts and a second salt-depleted glycol solution.

In stage d), the precipitated salts can be separated from the glycol solution by means of at least one of the following techniques: filtration, centrifugation, ultrasonic separation.

Before stage c), the glycol-enriched solution obtained in stage b) can be cooled or heated to a temperature ranging between 30° C. and 150° C.

In stage a), said solution can be expanded to a pressure ranging between 0.1 MPa and 2 MPa abs., and in stage b), distillation can be carried out at atmospheric pressure.

The depleted glycol solution obtained in stage e) can be used to heat the hydrocarbon-poor solution obtained in stage a).

The method according to the invention can comprise the following stages:

g) cooling the vapour containing water and hydrocarbons obtained in stage b) to obtain steam, a liquid hydrocarbon phase and an aqueous phase, h) sending part of the aqueous phase obtained in stage g) to the top of the distillation column, i) feeding the vaporized water obtained in stage c) into said distillation column, j) combining a second part of the glycol-enriched solution obtained in stage b) with the salt-depleted glycol solution obtained in stage d), k) feeding water into the salt-depleted glycol solution obtained in stage d).

The glycol can consist of a compound selected from the group comprising monoethylene glycol, diethylene glycol, triethylene glycol and tetraethylene glycol. The salts can comprise at least one of the following compounds: sodium chloride, potassium chloride, calcium chloride and sodium bicarbonate, sodium sulfate, potassium sulfate, calcium sulfate.

BRIEF DESCRIPTION OF THE FIGURES

Other features and advantages of the invention will be clear from reading the description hereafter, given by way of non limitative example, with reference to the accompanying drawings wherein.

DETAILED DESCRIPTION

A natural gas from a petroleum production well is transported by circulation in lines to a processing plant, for example a dehydration, deacidizing and/or gasoline recovery plant. In order to prevent hydrate formation, glycol is injected into the lines carrying the natural gas. Before being processed, the natural gas in gaseous form is separated from the aqueous glycol solution, for example by means of a separation drum.

Figure 1:
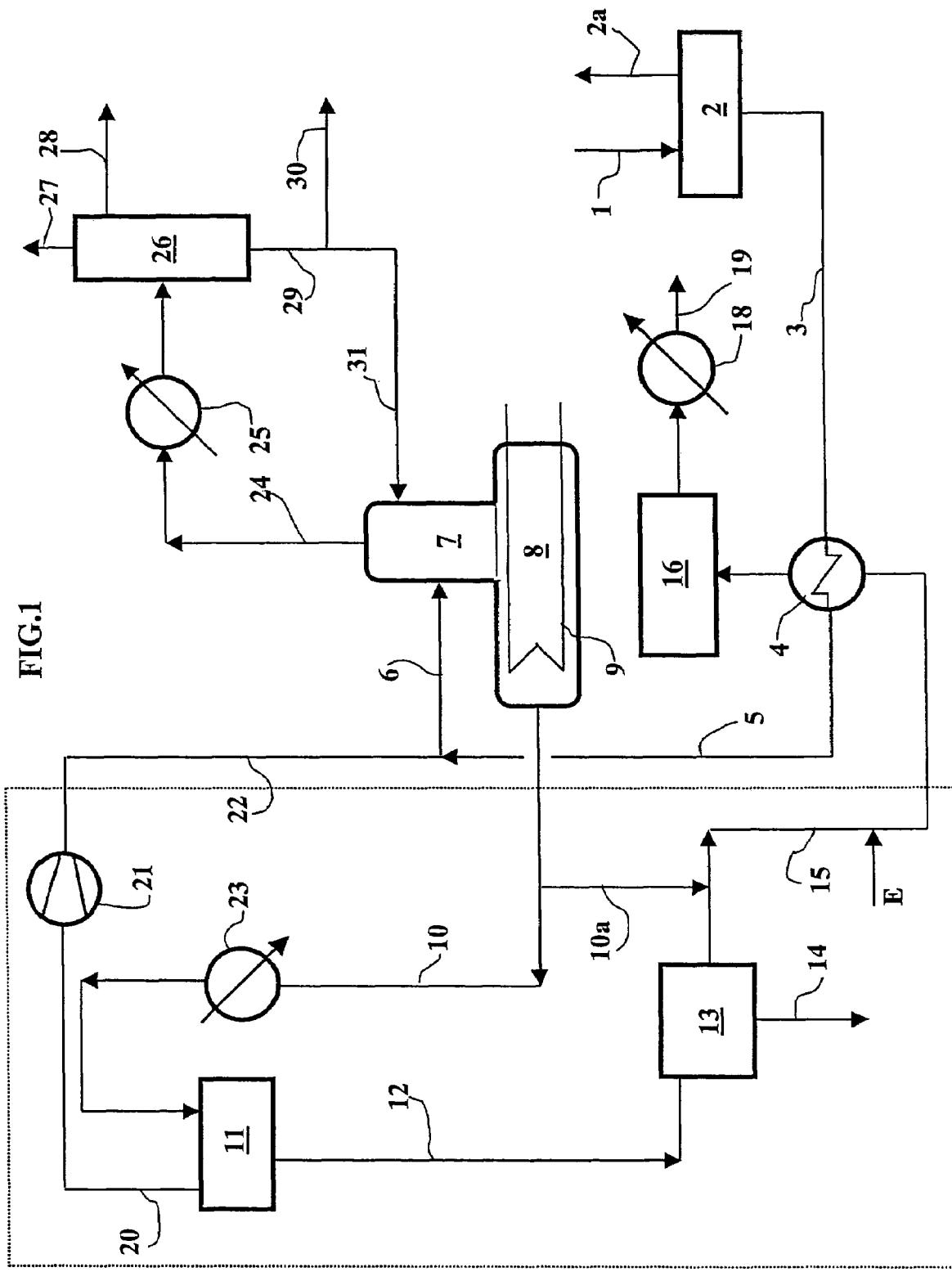
FIG. 1 diagrammatically shows the method according to the invention.

In FIG. 1, the aqueous glycol solution flows in through line (1). The glycol (1) containing water and salts is fed into a flash drum (2) where it releases through line (2a) the hydrocarbons coabsorbed upon contact with the natural gas. Drum (2) can work between 0.1 MPa and 2 MPa abs., preferably between 0.1 and 0.6 MPa abs.

The expanded glycol discharged through line (3) is heated in an exchanger (4) before it is fed through lines (5) and (6) into a regeneration column (7). Column (7) consists of a distillation column provided with a reboiler (8) at the bottom of the column and with a line (31) carrying a reflux liquid to the top of the column. Column (7) is provided with plates, random or stacked packings. Column (7) can work at atmospheric pressure. As a result of the reboiling heat provided by heating element (9) and of the distillation effect in column (7), a vapour is produced at the top of the column, mainly consisting of water and of a smaller proportion of hydrocarbons.

The vapour is discharged from column (7) through line (24). After cooling of this vapour in a heat exchanger (25), vapour, a liquid hydrocarbon phase and an aqueous phase are separated in drum (26) and respectively discharged through lines (27), (28) and (29). Part of the aqueous phase is sent through line (31) into column (7) as reflux, the remaining part being discharged through line (30).

The glycol recovered at the bottom of reboiler (8) is heated or cooled in exchanger (23) before it is fed into capacity (11) through line (10). Exchanger (23) allows to adjust the temperature, for example between 30° C. and 150° C., at which the salts are likely to precipitate. Part of the glycol circulating in line (10) can be withdrawn through line (10a), then mixed with the solution circulating in line (15). The glycol flows from reboiler (8) to capacity (11) by pressure difference. Capacity (11) is connected to vacuum pump (21) by line (20). Vacuum pump (21) allows capacity (11) to be placed under vacuum, i.e. to maintain capacity (11) at a pressure below the atmospheric pressure, for example below 90,000 Pa abs., preferably below 50,000 Pa abs. or 20,000 Pa abs. This pressure is selected notably as a function of the amounts of dissolved salts and water contained in the glycol solution, of the temperature of the glycol solution and of the nature of the salts. In capacity (11), under the effect of the temperature adjustment and of the vacuum, part of the water vaporizes with a small amount of glycol. The water vaporized in capacity (11) is pumped by pump (21), then sent through line (22) into reboiler (8) of the regeneration column. Lowering of the water content and adjustment of the temperature allow precipitation of the dissolved salts in the aqueous glycol solution at the level of capacity (11).

The solution containing the crystallized salts is discharged from capacity (11) through line (12) and it is sent to a separation device (13). The mixture can flow by gravity from capacity (11) into separation device (13) thanks to the level difference between these two elements. The lower the pressure in capacity (11), the greater the level difference between capacity (11) and separation device (13). Device (13) separates the precipitated salts from the rest of the solution. The salts are collected through line (14). The aqueous glycol solution freed of part of its salts is discharged from device (13) through line (15).

The salts remaining in the solution circulating in line (15) are at equilibrium, i.e. a change in the thermodynamic conditions could cause precipitation of the salts. In order to prevent precipitation of the salts in line (15), water can be injected by means of line (E). It is also possible to introduce part of the glycol circulating in line (10) into line (15) by means of line (10a). Thus, the remaining salts are not likely to precipitate because the water content of the solution circulating in line (15) has been increased.

The solution circulating in line (15) is heated or cooled in heat exchanger (4) before being stored in capacity (16). The glycol solution is discharged from capacity (16) through line (19) possibly after cooling in exchanger (18), then it is injected into a line carrying a natural gas from a production well.

Separation device (13) can consist of a filtration device (filtration on filtering media or precoat), a centrifugation device (centrifuge or cyclone), an ultrasonic separation device or a combination of these techniques.

Figure 2:
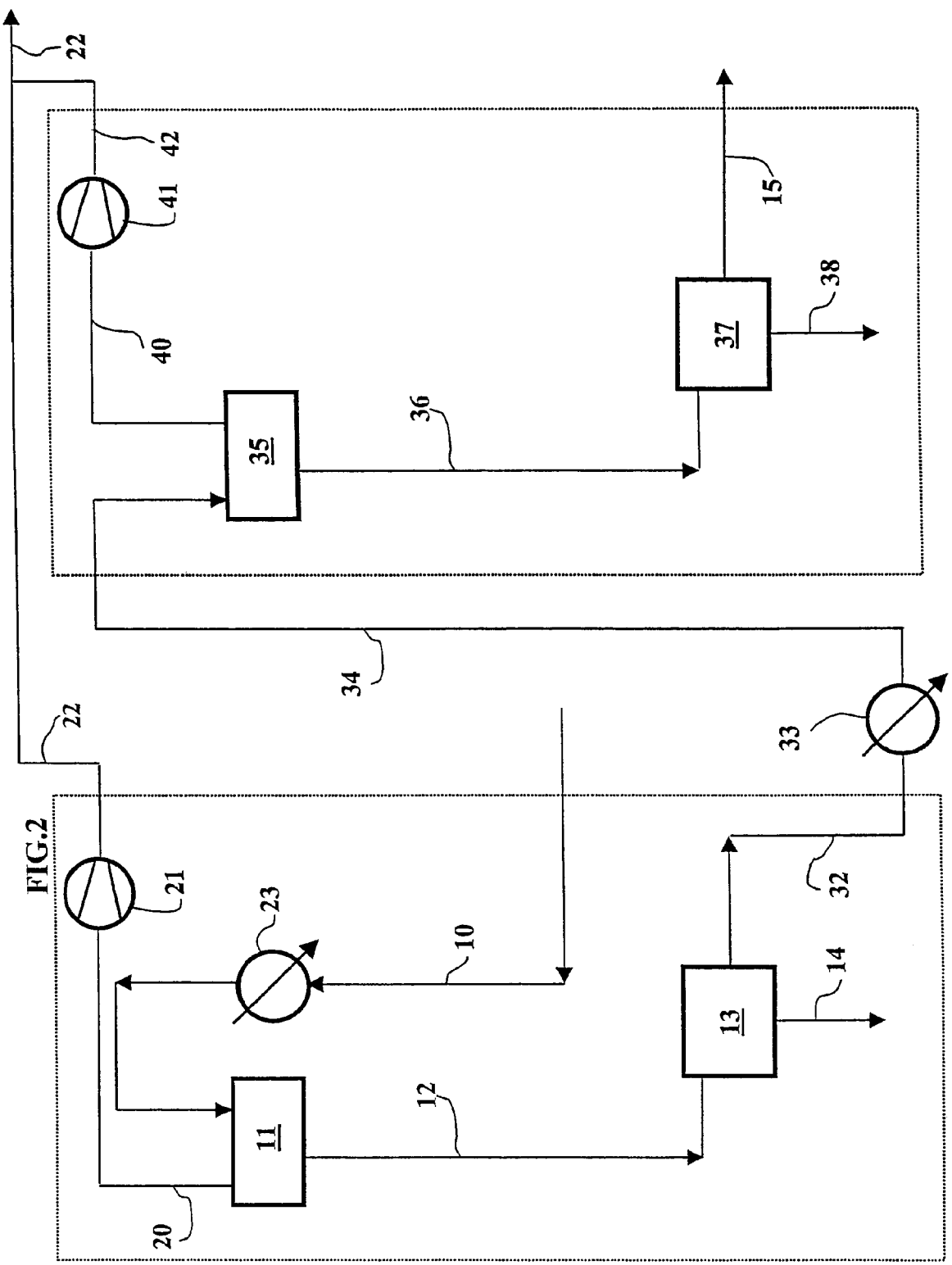
FIGS. 2 and 3 diagrammatically show variants of the method according to the invention.

FIG. 2 shows a variant of part of the method according to FIG. 1. The method according to FIG. 2 replaces the part of the method of FIG. 1 contained in the rectangle in dotted line. In FIGS. 1 and 2, identical reference numbers designate the same elements.

The method part shown in FIG. 2 comprises two salt precipitation and separation stages in series.

The glycol collected at the bottom of the regeneration column flows in through line (10), for example at atmospheric pressure. It is heated or cooled, for example to a temperature ranging between 30° C. and 150° C., in heat exchanger (23), then fed into capacity (11). Capacity (11) is connected to vacuum pump (21) by line (20). Vacuum pump (21) allows capacity (11) to be placed under vacuum by maintaining capacity (11) at a pressure below 90,000 Pa abs., preferably below 50,000 Pa. The water vaporized in capacity (11) is pumped by pump (21), then sent through line (22) to reboiler (8) of regeneration column (7). The solution containing the crystallized salts is discharged from capacity (11) through line (12) and sent to a separation device (13). Device (13) separates the precipitated salts from the rest of the solution. The salts are recovered through line (14). The aqueous glycol solution at least partly freed of its salts is discharged from device (13) through line (32).

The solution circulating in line (32) is heated or cooled, for example to a temperature ranging between 30° C. and 150° C., by heat exchanger (33), then sent through line (34) into capacity (35). Capacity (35) is connected to vacuum pump (41) by line (40). Vacuum pump (41) allows capacity (34) to be placed under vacuum by maintaining capacity (34) at a pressure below 50,000 Pa abs., preferably below 20,000 Pa abs. The water vaporized in capacity (35) is pumped by pump (41) and sent through lines (42) and (22) to reboiler (8) of the regeneration column. The mixture of crystallized salts and solution is discharged from capacity (35) through line (36) and sent to a separation device (37). Device (37) separates the precipitated salts from the rest of the solution. The salts are collected through line (38). The aqueous glycol solution partly freed of its salts is discharged from device (37) through line (15) and sent to storage capacity (16). This particular device allows to reduce more significantly the residual amount of salts present in the regenerated glycol solution.

Figure 3:
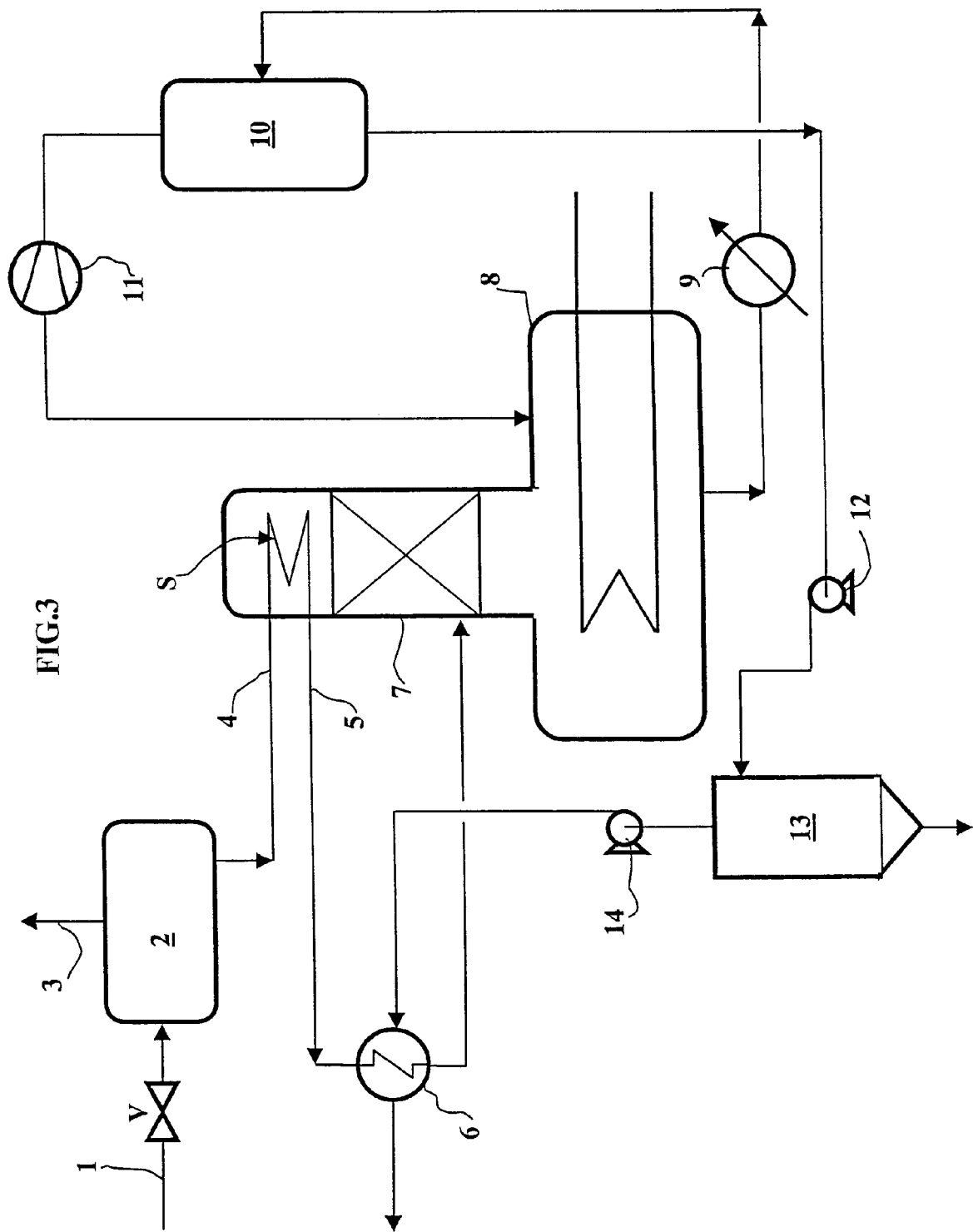

A numerical example of the operating conditions of the method according to the invention is given in connection with the method diagrammatically shown in FIG. 3.

A rich glycol (MEG+water+salts) flowing in through line (1) has to be processed in order to concentrate it at 90% by weight and to eliminate part of the salts it contains so as to prevent salt deposition on certain elements of the regeneration device and to limit corrosion phenomena. The flow rate of the rich glycol to be processed is 12,500 kg/h, its concentration is 55% by weight of MEG and it contains 0.3% by weight of salts. It is available at 30° C. and at 0.6 MPa abs.

The rich glycol (1) is expanded to 0.5 MPa abs. by valve (V), then it is sent to a flash drum (2) where the hydrocarbons dissolved in the glycol are vaporized, then discharged through line (3). The rich glycol flowing from drum (2) through line (4) is heated in reflux coil (S) of regeneration column (7), then it is fed through line (5) into exchanger (6) to be heated to a temperature of about 75° C., and fed to regeneration column (7). Reboiler (8) works at atmospheric pressure at a temperature of 116.5° C., the glycol is then concentrated at 70% by weight and, under such conditions, there is no or little risk of precipitation of the salts in the reboiler. The partly regenerated glycol is then heated to a temperature of 131° C. in exchanger (9) and fed into capacity (10). Capacity (10) is maintained under vacuum at a pressure of 80,000 Pa abs. The operating conditions of this capacity have been so selected as to concentrate the glycol to up to 90% by weight and to cause precipitation of the salts. The water vaporized in capacity (10) is pumped by pump (11) and sent back to reboiler (8). The glycol solution concentrated at 90% by weight and containing crystallized salts is sent by pump (12) to a centrifugal separation device (13). The regenerated glycol freed of its salts is then pumped (14) and sent to exchanger (6) to be cooled by thermal exchange with the glycol circulating in line (5).

The invention claimed is:

1. A method of regenerating a glycol solution containing water, hydrocarbons and dissolved salts, comprising the following stages:
   a) expanding said solution so as to release hydrocarbons and to obtain a hydrocarbon-poor solution,
   b) distilling in a distillation column the hydrocarbon-poor solution obtained in stage a) to obtain a glycol-enriched solution and a vapor comprising water and hydrocarbons,
   c) placing under vacuum a first part of the glycol-enriched solution obtained in stage b) under a pressure below 90,000 Pa abs. to obtain vaporized water and a glycol solution comprising precipitated salts, and
   d) separating the precipitated salts from the glycol solution obtained in stage c) to obtain precipitated salts and a salt-depleted glycol solution, wherein the salts comprise at least one compound selected from the group consisting of sodium chloride, potassium chloride, calcium chloride, sodium bicarbonate, sodium sulfate, potassium sulfate and calcium sulfate.

2. A method as claimed in claim 1, further comprising the following stages:
   e) placing under vacuum the salt-depleted glycol solution obtained in stage d) under a pressure below 50,000 Pa abs. to obtain vaporized water and a glycol solution comprising precipitated salts,
   f) separating the precipitated salts from the glycol solution obtained in stage e) to obtain precipitated salts and a second salt-depleted glycol solution.

3. A method as claimed in claim 1 wherein, in stage d), the precipitated salts are separated from the glycol solution by means of at least one of the following techniques: filtration, centrifugation, ultrasonic separation.

4. A method as claimed in claim 1 wherein, before stage c), the glycol-enriched solution obtained in stage b) is cooled to a temperature ranging between 30° C. and 150° C.

5. A method as claimed in claim 1 wherein, before stage c), the glycol-enriched solution obtained in stage b) is heated to a temperature ranging between 30° C. and 150° C.

6. A method as claimed in claim 1 wherein, in stage a), said solution is expanded to a pressure ranging between 0.1 MPa and 2 MPa abs. and wherein, in stage b), distillation is performed at atmospheric pressure.

7. A method as claimed in claim 1, wherein the following stages are further carried out:
   cooling the vapor containing water and hydrocarbons obtained in stage b) to obtain steam, a liquid hydrocarbon phase and an aqueous phase, and
   sending part of the aqueous phase to the top of the distillation column.

8. A method as claimed in claim 1, wherein the following stage is further carried out:
   feeding the vaporized water obtained in stage c) into said distillation column.

9. A method as claimed in claim 1, wherein the following stage is further carried out:
   combining a second part of the glycol-enriched solution obtained in stage b) with the salt-depleted glycol solution obtained in stage d).

10. A method as claimed in claim 1, wherein the following stage is further carried out:
    feeding water into the salt-depleted glycol solution obtained in stage d).

11. A method of regenerating a glycol solution containing water, hydrocarbons and dissolved salts, comprising the following stages:
    a) expanding said solution so as to release hydrocarbons and to obtain a hydrocarbon-poor solution,
    b) distilling in a distillation column the hydrocarbon-poor solution obtained in stage a) to obtain a glycol-enriched solution and a vapor comprising water and hydrocarbons,
    c) placing under vacuum a first part of the glycol-enriched solution obtained in stage b) under a pressure below 90,000 Pa abs. to obtain vaporized water and a glycol solution comprising precipitated salts,
    d) separating the precipitated salts from the glycol solution obtained in stage c) to obtain precipitated salts and a salt-depleted glycol solution,
    e) placing under vacuum the salt-depleted glycol solution obtained in stage d) under a pressure below 50,000 Pa abs. to obtain vaporized water and a glycol solution comprising precipitated salts, and
    f) separating the precipitated salts from the glycol solution obtained in stage e) to obtain precipitated salts and a second salt-depleted glycol solution, wherein the second salt-depleted glycol solution f) heats the hydrocarbon-poor solution obtained in stage a).

12. A method of regenerating a glycol solution containing water, hydrocarbons and dissolved salts, comprising the following stages:
    a) expanding said solution so as to release hydrocarbons and to obtain a hydrocarbon-poor solution,
    b) distilling in a distillation column the hydrocarbon-poor solution obtained in stage a) to obtain a glycol-enriched solution and a vapor comprising water and hydrocarbons,
    c) placing under vacuum a first part of the glycol-enriched solution obtained in stage b) under a pressure below 90,000 Pa abs. to obtain vaporized water and a glycol solution comprising precipitated salts, and
    d) separating the precipitated salts from the glycol solution obtained in stage c) to obtain precipitated salts and a salt-depleted glycol solution, wherein the glycol consists of a compound selected from the group consisting of monoethylene glycol, diethylene glycol and triethylene glycol.

* * * * *